(12) United States Patent
Whelan et al.

(10) Patent No.: US 11,305,108 B2
(45) Date of Patent: Apr. 19, 2022

(54) IMPLANTABLE MEDICAL LEAD DEVICES AND SYSTEMS HAVING BALANCED CLOCKED CONDUCTOR POSITIONS

(71) Applicant: MEDTRONIC, INC., Minneapolis, MN (US)

(72) Inventors: Vincent M. Whelan, New Brighton, MN (US); Jorge Alvarado, Aibonio, PR (US); Adam J. Rivard, Blaine, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 215 days.

(21) Appl. No.: 16/704,594

(22) Filed: Dec. 5, 2019

(65) Prior Publication Data

US 2021/0170165 A1 Jun. 10, 2021

(51) Int. Cl.
*A61N 1/05* (2006.01)
*A61N 1/36* (2006.01)
*A61N 1/362* (2006.01)
*A61N 1/39* (2006.01)

(52) U.S. Cl.
CPC .............. *A61N 1/05* (2013.01); *A61N 1/362* (2013.01); *A61N 1/3605* (2013.01); *A61N 1/39* (2013.01)

(58) Field of Classification Search
CPC .... A61N 1/0472; A61N 1/048; A61N 1/0448; A61N 1/05; A61N 1/3605; A61N 1/362; A61N 1/39; A61N 1/3752
See application file for complete search history.

(56) References Cited

U.S. PATENT DOCUMENTS

| | | |
|---|---|---|
| 7,239,923 B1 | 7/2007 | Tockman et al. |
| 8,543,222 B1 | 9/2013 | Sochor |
| 9,101,755 B2 | 8/2015 | Pianca |
| 9,399,127 B2 | 7/2016 | Flowers et al. |
| 9,878,148 B2 | 1/2018 | Leven et al. |
| 2005/0027341 A1 | 2/2005 | Schrom |
| 2012/0065699 A1 | 3/2012 | Bedenbaugh |
| 2012/0316615 A1 | 12/2012 | Digiore et al. |
| 2014/0005599 A1 | 1/2014 | Sage |
| 2014/0316502 A1 | 10/2014 | Seeley |
| 2017/0312500 A1 | 11/2017 | Shoberg et al. |

(Continued)

OTHER PUBLICATIONS

Kollman, D.T. et al., "ICD Lead Failure Detection Through High Frequency Impedance", IEEE Engineering in Medicine and Biology Society, Aug. 26, 2014, pp. 6487-6492.

(Continued)

*Primary Examiner* — Paula J Stice
(74) *Attorney, Agent, or Firm* — Withers & Keys, LLC

(57) ABSTRACT

Implantable medical lead devices such as leads and lead extensions include conductors within the lead device body that interconnect proximal and distal electrical connectors and that have balanced clocked positions. The balanced clocked positions may be achieved by separating a first conductor from a second conductor by an adequate amount, where the first conductor has a length as measured from a given point along the lead to the end of the conductor that is most similar to the length of the second conductor as measured in the same manner. The balanced clocked position of conductor pairings based on similarity of length may provide benefits such as reducing the tendency of the lead to curve when one or more layers of the lead body are being injection molded around the conductors.

22 Claims, 4 Drawing Sheets

(56) References Cited

U.S. PATENT DOCUMENTS

| | | |
|---|---|---|
| 2018/0366238 A1 | 12/2018 | Richter et al. |
| 2019/0060633 A1 | 2/2019 | Skubitz et al. |
| 2019/0060634 A1 | 2/2019 | Skubitz et al. |

OTHER PUBLICATIONS

PCT/US2020/063276 International Search Report and Written Opinion, dated Mar. 17, 2021.

IMPLANTABLE MEDICAL LEAD DEVICES AND SYSTEMS HAVING BALANCED CLOCKED CONDUCTOR POSITIONS

TECHNICAL FIELD

Embodiments relate to implantable medical lead devices and systems that include conductors having balanced clocked conductor positions.

BACKGROUND

Implantable medical systems provide medical therapy by producing electrical stimulation signals that are delivered to a target site within the body. An implantable stimulation device that produces the electrical stimulation signals is typically implanted at a location of convenience within the body of the patient that is capable of accommodating the physical size of the device. This implantation location of the implantable stimulation device may be at some distance from the target stimulation site within the body. Therefore, an implantable medical lead device is also implanted to deliver the electrical stimulation signals to the target site.

The implantable medical lead device may take various forms. For instance, for a relatively shorter distance from the implantable medical device to the target stimulation site, the implantable medical lead device may be an implantable medical lead. The implantable medical lead has a proximal end that couples to the implantable stimulation device and a distal end that has electrodes and that is located at the target site to deliver the electrical signals from the electrodes to the target site. For a relatively longer distance from the implantable medical device to the target stimulation site that exceeds the reach of an implantable medical device alone, multiple implantable medical lead devices may be included. A first implantable medical lead device in the form of an implantable medical lead extension may be coupled between a second implantable medical lead device in the form of the implantable medical lead and the implantable stimulation device. The implantable medical lead extension has proximal end that couples to the implantable stimulation device and a distal end that includes a distal housing that couples to the proximal end of the implantable medical lead. The implantable medical lead extension carries the electrical stimulation signals between the implantable stimulation device and the implantable medical lead.

In either case, the proximal end of the implantable medical lead device is inserted into a lead bore of the implantable stimulation device in order to couple electrical connectors on the proximal end to electrical contacts within the lead bore. This can present a challenge for conventional implantable medical lead devices that are created by using injection molding to form the lead body at the proximal end where the proximal contacts are located. Due to conventional conductor routing within the implantable medical lead device, the injection molding may result in a curvature of the proximal end that complicates the insertion of the proximal end into the lead bore.

SUMMARY

Embodiments address issues such as these and others by providing implantable medical lead devices that include balanced clocked conductor positions. Examples of balance clocked conductor positions include at least one pair conductors of a similar length as measured from a given longitudinal location along the lead to the respective electrical connectors coupled to the conductors where the at least one pair of conductors are in clocked positions within the body of the lead so that the angle of separation between them is greater than 135 degrees. Other examples of balanced clocked conductor positions include at least one pair of conductors of a similar length as measured from a given longitudinal location along the lead to the respective electrical connectors coupled to the conductors where the at least one pair of conductors are in clocked positions within the body of the lead so that the angle of separation between them is equal to at least a quantity equal to 180 degrees less a second quantity equal to 360 degrees divided by a total number of conductors present within the lead device body. These balanced clocked conductor positions assist in reducing the tendency of the end of the implantable medical device to become curved due to injection molding. Clocked positions in general as used herein refer to positions spaced around a looped layout such as circular, elliptical, and the like.

Embodiments provide an implantable medical lead device that includes a lead device body and at least four proximal electrical connectors located on a proximal end of the lead device body and separated longitudinally. The implantable medical lead device further includes at least four distal electrical connectors located on a distal end of the lead device body and at least four conductors within the lead device body. Each conductor of the at least four conductors interconnects a corresponding proximal electrical connector of the at least four electrical proximal connectors to a corresponding distal electrical connector of the at least four distal electrical connectors. Each of the at least four conductors has a length as measured from a given longitudinal position along the lead device body where the at least four conductors are present to the corresponding proximal electrical connector of each conductor. The length of a first conductor of the at least four conductors is most similar among the at least four conductors to the length of a second conductor of the at least four conductors. The first conductor and the second conductor are clocked in positions that provide an angular separation between the first conductor and the second conductor of at least 135 degrees.

Embodiments provide an implantable medical system that includes an implantable medical stimulator device that includes a header having a lead bore and electrical contacts within the lead bore. The implantable medical system includes an implantable medical lead device that includes a lead device body. At least four proximal electrical connectors are located on a proximal end of the lead device body and are separated longitudinally. The proximal end being located within the lead bore such that the at least four proximal electrical connectors are in contact with corresponding electrical contacts present within the lead bore. At least four distal electrical connectors are located on a distal end of the lead device body, and at least four conductors are within the lead device body. Each conductor of the at least four conductors interconnects a corresponding proximal electrical connector of the at least four proximal electrical connectors to a corresponding distal electrical connector of the at least four distal electrical connectors. Each of the at least four conductors has a length as measured from a given longitudinal position along the lead device body where the at least four conductors are present to the corresponding proximal electrical connector of each conductor. The length of a first conductor of the at least four conductors is most similar among the at least four conductors to the length of a second conductor of the at least four conductors. The first conductor and the second conductor are clocked in positions that provide an angular separation between the first conductor and the second conductor of at least 135 degrees.

Embodiments provide an implantable medical lead device that includes a lead device body and at least five proximal electrical connectors located on a proximal end of the lead device body and separated longitudinally. At least five distal electrical connectors are located on a distal end of the lead device body, and at least five conductors are within the lead device body. Each conductor of the at least five conductors interconnects a corresponding proximal electrical connector of the at least five proximal electrical connectors to a corresponding distal electrical connector of the at least five distal electrical connectors. Each of the at least five conductors has a length as measured from a given longitudinal position along the lead device body where the at least five conductors are present to the corresponding proximal electrical connector. The length of a first conductor of the at least five conductors is most similar among the at least five conductors to the length of a second conductor of the at least five conductors. The first and second conductors are clocked in positions that provide an angular separation between the first conductor and the second conductor of at least a quantity equal to 180 degrees less a second quantity equal to 360 degrees divided by a total number of conductors present within the lead device body.

Embodiments provide an implantable medical system that includes an implantable medical stimulation device that includes a header having a lead bore and electrical contacts within the lead bore. The implantable medical system includes an implantable medical lead device that includes a lead device body and at least five proximal electrical connectors located on a proximal end of the lead device body and separated longitudinally. The proximal end is located within the lead bore such that the at least five proximal electrical connectors are in contact with corresponding electrical contacts present within the lead bore. At least five distal electrical connectors are located on a distal end of the lead device body and at least five conductors are within the lead device body. Each conductor of the at least five conductors interconnects a corresponding proximal electrical connector of the at least five proximal electrical connectors to a corresponding distal electrical connector of the at least five distal electrical connectors. Each of the at least five conductors has a length as measured from a given longitudinal position along the lead device body where the at least five conductors are present to the corresponding proximal electrical connector of each conductor. The length of a first conductor of the at least five conductors is most similar among the at least five conductors to the length of a second conductor of the at least five conductors. The first conductor and the second conductor are clocked in positions that provide an angular separation between the first conductor and the second conductor of at least a quantity equal to 180 degrees less a second quantity equal to 360 degrees divided by a total number of conductors present within the lead device body.

Embodiments provide a method of providing an implantable medical lead device that involve providing a lead device body and providing at least four proximal electrical connectors located on a proximal end of the lead device body and separated longitudinally. The method further involves providing at least four distal electrical contacts located on a distal end of the lead device body and inserting at least four conductors within the lead device body. Each conductor of the at least four conductors interconnects a corresponding proximal electrical connector of the at least four proximal electrical connectors to a corresponding distal electrical connector of the at least four distal electrical connectors. Each of the at least four conductors have a length as measured from a given longitudinal position along the lead device body where the at least four conductors are present to the corresponding proximal electrical connector of each conductor. The length of a first conductor of the at least four conductors is most similar among the at least four conductors to the length of a second conductor of the at least four conductors. The first conductor and the second conductor are clocked in positions that provide an angular separation between the first conductor and the second conductor of at least 135 degrees.

Embodiments provide a method of providing an implantable medical lead device that involves providing a lead device body and providing at least five proximal electrical connectors located on a proximal end of the lead device body and separated longitudinally. The method further involves providing at least five distal electrical connectors located on a distal end of the lead device body and inserting at least five conductors within the lead device body. Each conductor of the at least five conductors interconnects a corresponding proximal electrical connector of the at least five proximal electrical connectors to a corresponding distal electrical connector of the at least five distal electrical connectors. Each of the at least five conductors has a length as measured from a given longitudinal position along the lead device body where the at least five conductors are present to the corresponding proximal electrical connector of each conductor. The length of a first conductor of the at least five conductors is most similar among the at least five conductors to the length of a second conductor of the at least five conductors. The first conductor and the second conductor are clocked in positions that provide an angular separation between the first conductor and the second conductor of at least a quantity equal to 180 degrees less a second quantity equal to 360 degrees divided by a total number of conductors present within the lead device body.

DETAILED DESCRIPTION

Embodiments provide implantable medical lead devices such as leads and lead extensions that include conductors with balanced clocked positions that reduce the tendency of the end of the lead to curve upon being injection molded. One or more pairs of conductors of similar length as measured from a point of reference to the end of the conductors of the pair are arranged to be in balanced clocked positions within the lead. Embodiments provide various examples of balanced clocked conductor positions, such as maintaining at least 135 degrees of separation of the balanced clocked conductor positions of the two conductors of the pair in one example. As another example, embodiments may maintain a separation of the balanced clocked conductor positions of the two conductors of the pair by at least a quantity equal to 180 degrees less one average clocked position separation, where the average clocked position separation may be found as a second quantity equal to 360 degrees divided by the number of conductors that are present within the lead device.

Figure 1:
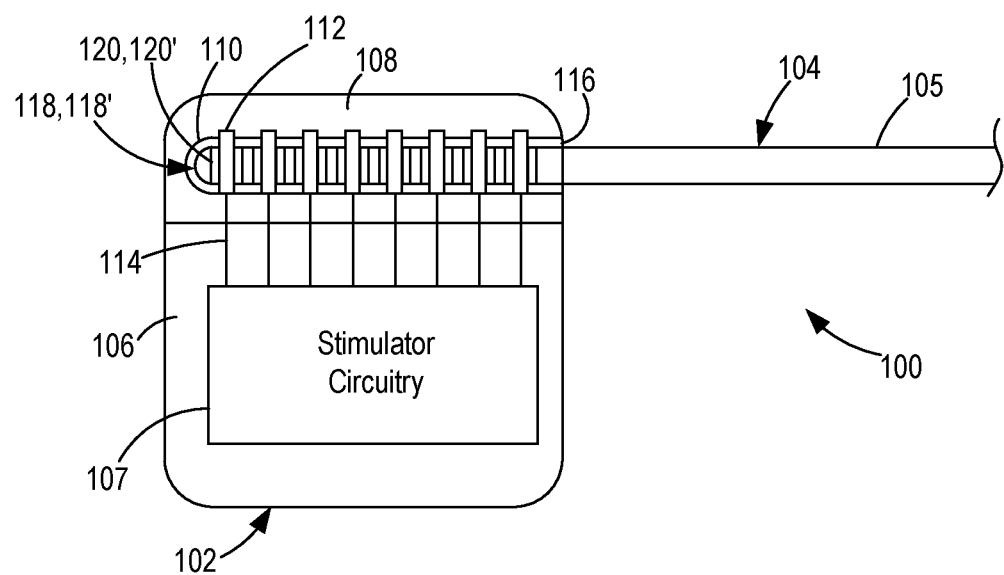
FIG. 1 shows an example of an implantable medical system including a proximal end of an implantable medical lead device.

An example of an implantable medical device system 100 that may include embodiments of the balanced clocked conductor positions of an implantable medical lead device 104 is shown in FIG. 1. The implantable medical system 100 includes an implantable medical stimulation device 102. In this example, the implantable medical stimulation device 102 includes a housing 106 that includes stimulator circuitry 107 that produces the electrical stimulation signals. The implantable medical stimulation device 102 of this example also includes a header 108 mounted atop the housing 106, where the header 108 includes a lead bore 110 with opening 116 where the proximal end 118 (if lead device 104 is a lead extension), 118' (if lead device 104 is a lead) of lead device 104 is inserted.

Electrical stimulation signals from the stimulator circuitry 107 travel inside the housing 107 to electrical contacts 112 in the lead bore 110 of the header 108. An electrically conductive path 114 for the electrical stimulation signals is provided for each output channel of the stimulator circuitry 107. The housing may be hermetically sealed to prevent fluids from entering the housing 106, and in that case, the electrically conductive path may include a hermetic feed-through where the path 114 transitions from inside the housing 106 to inside the header 108. The path 114 for each channel of the stimulator circuitry 107 continues to corresponding electrical contacts 112.

Once the proximal end 118, 118' of the implantable medical lead device 104 is fully inserted into the lead bore 110, proximal electrical contacts 120 (if lead device 104 is a lead extension), 120' (if lead device 104 is a lead) in the form of rings in this example come into physical contact with the electrical connectors 112. Electrical conductors within the body 105 of the lead device 104 and electrically connected to corresponding connectors 120, 120' then carry the stimulation signals to the distal end of the lead device 104. The body 105 may be constructed of biocompatible materials including various polymers such as polyurethane and the like to provide flexibility while also providing protection of the conductors from external conditions.

The example of FIG. 1 shows a total of eight separate conductive paths, eight separate contacts, and eight separate connectors. It will be appreciated by one of ordinary skill in the art that the number of conductive paths, contacts, and connectors may vary from those shown in FIG. 1 while still implementing balanced clocked conductor positions within the lead device 104.

Figure 2:
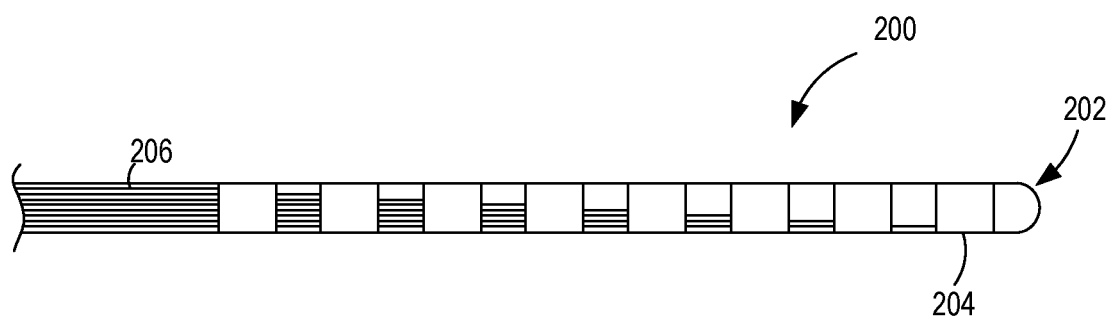
FIG. 2 shows a distal end of an implantable medical lead.

FIG. 2 shows an example of a distal end 202 of an implantable medical lead 200, which is an example of the implantable medical lead device 104 of FIG. 1. The distal end includes distal electrical connectors 204 in the form of ring electrodes that are electrically coupled to the distal portion 206 of conductors within the lead 200. The lead 200 is implanted so that the distal electrodes 204 are positioned at the target stimulation site within the body of the patient to deliver the electrical stimulations signals. While the distal portion 206 of the conductors are shown as approaching the electrodes in a stair-stepped manner, it will be appreciated by those of ordinary skill in the art that the conductors of the distal end 200 may instead be in the same balanced clocked positions as the conductors at the proximal end 118' of the lead 200 as discussed in detail below in relation to FIGS. 4-6. Indeed, if the conductors 206 maintain the same position as the balanced clocked positions of the proximal end 118' of the lead 200 and the distal electrodes are order in the same manner as the proximal connectors 120', then the distal portion of the conductors 206 will also be in balanced clocked positions.

Figure 3:
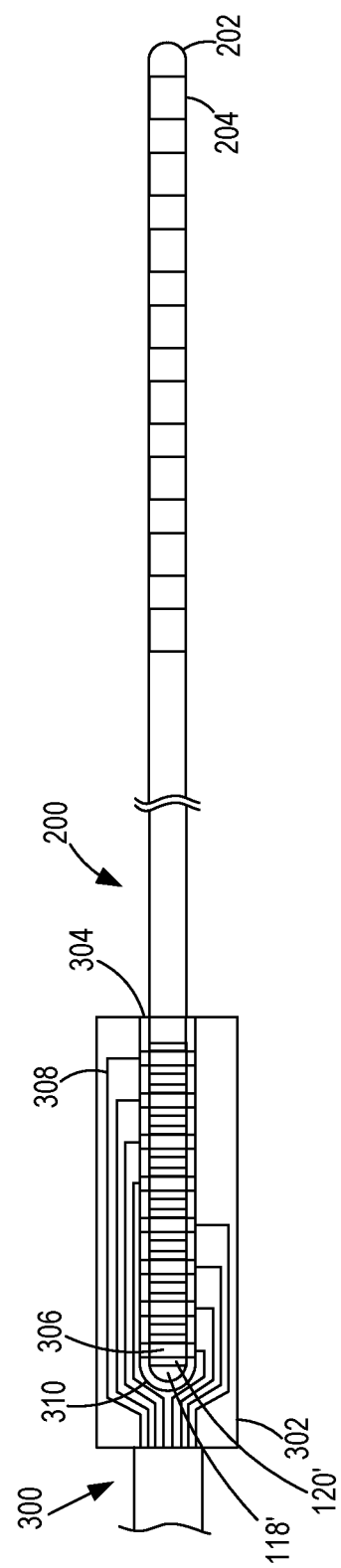
FIG. 3 shows a distal end of an implantable medical lead extension connected to a proximal end of the implantable medical lead.

FIG. 3 shows an example of a distal end of an implantable medical lead extension 300, which is an example of the implantable medical lead device 104 of FIG. 1. The distal end includes a distal housing 302 that contains distal contacts 306 within a lead bore 310. The distal contacts 306 are electrically coupled to a distal portion 308 of conductors within the lead extension 300.

The lead extension 300 is implanted so that the distal end is positioned at location of convenience for receiving the proximal end 118' of the implantable medical lead 200 into the lead bore 310 through an opening 304 in the housing 302. The proximal connectors 120' of the lead 200 physically engage distal electrical connectors 306 of the lead extension 300 that are located within the lead bore 310 and take the form of electrical contacts. This effectively extends the pathway from the electrical connectors 112 of the implantable stimulation device 102 from FIG. 1 to the distal electrodes 204 of the lead 200 of FIG. 2.

In this example shown in FIG. 3, balanced clocked conductors may be present in the proximal end 118 of the embodiment of the implantable medical lead extension 300 to reduce the tendency of curvature in the proximal end 118 to aid in the insertion of the proximal end 118 into the lead bore 110 of the implantable medical stimulation device 202. Alternatively or additionally, balanced clocked conductors may be present in the proximal end 118' of the embodiment of the implantable medical lead 200 to reduce the tendency of curvature in the proximal end 118' to aid in the insertion of the proximal end 118' into the lead bore 310 of the implantable medical lead extension 300.

Figure 4:
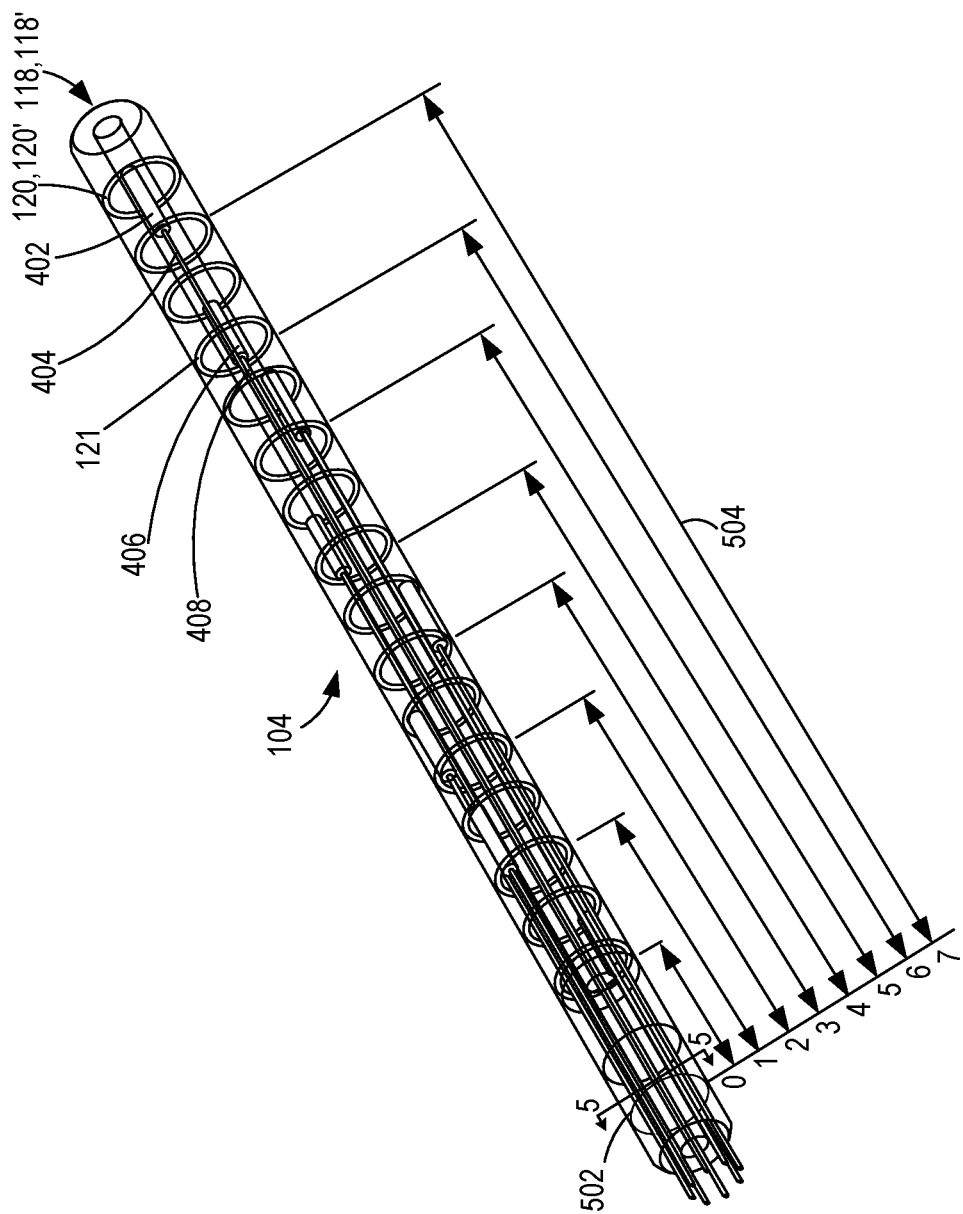
FIG. 4 shows an end of the implantable medical lead device and illustrates the example of balanced clocked conductor positions

FIG. 4 shows a perspective view of an example of a proximal end 118, 118' of the implantable medical lead device 104, whether the lead extension 300 or the lead 200. The lead body 105 from FIG. 1 is shown here in a translucent manner to reveal the details within the lead body 105. Here, the proximal portions of conductors of the lead device 104 are linear and are shown being present in balanced clocked positions within the lead device 104. As stated above, balanced clocked positions may be achieved in relation to any two conductors that are of most similar length to each other among the conductors of the lead device 104 as measured from a given point of reference along the lead device 104 to the corresponding proximal electrical connectors of the two conductors.

In this example, it can be seen that from a reference point 502 that is present at a given longitudinal position along the lead device body 105 where all eight conductors are present, each conductor has a length 504 as measured from the given reference point 502 to the corresponding electrical connector, in this case the proximal electrical connector located on the proximal end 118, 118' of the lead device 104. Each conductor length 504 is referenced to the conductor numbered from "0-"7". Here it can be seen that when starting from conductor "7", which corresponds to conductor 404 having attachment 402 to electrode 120, 120', the conductor with the most similar length to the length of conductor "7" as measured from given point 502 is conductor "6", which corresponds to conductor 408 having attachment 406 to electrode 121. Therefore, to provide the balanced clocked position of conductors "7" and "6", these conductors are separated from each other by some balanced amount.

It can also be seen that other conductors may similarly be paired. Conductor "5" is most similar in length as measured from the given reference point 502 to conductors "4" and "6", but since conductor "6" is paired with conductor "7" for purposes of positioning to achieve balanced clocked positions, conductor "5" may be paired with "conductor "4" and positioned to achieve balanced clocked positions. Conductor "3" is most similar in length as measured from the given reference point 502 to conductors "2" and "4", but since conductor "4" may be paired with conductor "5" and positioned to achieve balanced clocked positions, conductor "3" may be paired with "conductor "2" and positioned to achieve balanced clocked positions. Continuing with this scheme, conductors "1" and "0" may also be paired for positioning to achieve balanced clocked positions.

Figure 5:
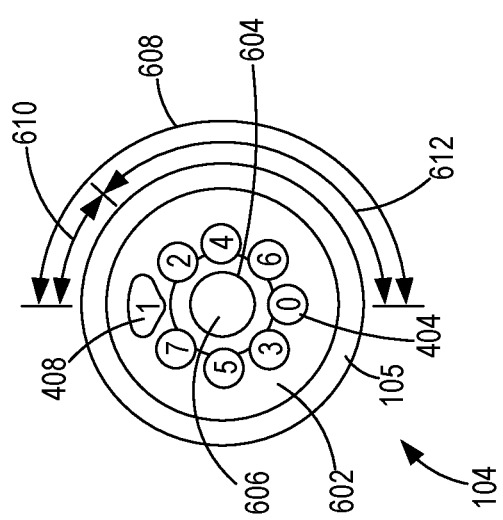
FIG. 5 shows a cross-sectional view taken laterally through the implantable medical lead device that further demonstrates the example of balanced clocked conductor positions.

The example shown in FIGS. 4 and 5 includes a total of eight separate conductors and corresponding connectors. As with FIG. 1, it will be appreciated by one of ordinary skill in the art that the number of conductors and corresponding connectors may vary from those shown in FIGS. 4 and 5 while still implementing balanced clocked conductor positions within the lead device 104.

As discussed above, the balanced amount of angular separation may be established in multiple ways and for varying numbers of conductors that may be present within the lead device 104. This angular separation of the example of FIG. 4 is further shown in the lateral cross-section of the lead device 104 in FIG. 5 which is taken through line 5-5 of FIG. 4 nearby the reference point 502 where all eight conductors are present and linear in their balanced clocked positions. Note that in the example of FIG. 5, the lead device 104 includes the lead body 105 providing an outer layer, an inner body 602 that contains the conductors and that is surrounded by the lead body 105, and a lumen body 604 that is surrounded by the inner body 602 and conductors and that establishes a lumen 606. It will be appreciated by one or ordinary skill in the art that the lead devices 104 may omit one or more of these layers and still provide the balanced clocked conductor positions.

In one example, the angular separation 608 of FIG. 5 that is between two conductors of most similar length when measured from the given reference point may range from 135 degrees to the maximum possible angular separation of 180 degrees regardless of the number of conductors. For instance, in one specific example of a medical lead 104 that has at least four conductors present, the angular separation 608 between the two conductors, e.g., conductors "7" and "6" that are of most similar length as measured from the given reference point, ranges anywhere from 135 degrees to 180 degrees. As shown in the example of FIG. 5, the angular separation 608 from center of conductor "7" to center of conductor "6" is a full 180 degrees. It can be seen that the same is true for the other three conductor pairings described above.

In another example, the balanced amount of angular separation may range from a quantity of angular separation 612 that is equal to at least a quantity equal to 180 degrees less a single average clocked position angular separation 610 up to the maximum possible angular separation of 180 degrees. The average single clocked position angular separation may be determined as a second quantity by dividing a full 360 degrees by the number of conductors present. For instance, in one specific example of a medical lead 104 that has at least five conductors present, the balanced amount of angular separation may range from a quantity of angular separation 612 that is equal to 180 degrees less a single average clocked position amount of angular separation 610 up to the maximum possible angular separation of 180 degrees. In the example shown in FIG. 5 with eight conductors "0"-"7", the balanced amount of angular separation may range from a quantity of angular separation 612 that is equal to [180 degrees less (360 degrees divided by 8=45 degrees)=135 degrees] up to the maximum possible angular separation of 180 degrees. Thus, for example, conductor "1" could swap places with conductor "2" or conductor "7" and the pairing of conductors "0" and "1" would remain in the range for being adequately balanced while the pairing of conductors "2" and "3" and the pairing of conductors "6" and "7" would also remain in the range for being adequately balanced.

While FIGS. 4 and 5 show an order of conductors looking distally and going clockwise as "7," "1," "2," "4," "6," "0," "3," "5," many other orders of conductors are also applicable and allow for balanced clocked conductor positions. For instance, an alternative order of conductors looking distally and going clockwise could be "7," "3," "5," "1," "6," "2," "4," "0." It will be appreciated that in both of these examples, "7" is paired with "6" to have balanced clocked positions while "5 is paired with "4," "3" is paired with "2," and "1" is paired with "0."

Furthermore, it will be appreciated that not all conductors present in the lead device 104 are required to have balanced clocked positions. For instance, in some cases multiple pairings of conductors having balanced clocked positions may provide adequate resistance to curving of the end even though one or more other conductors may not have balanced clocked positions.

Accordingly, lead devices 104 such as leads 200 and/or lead extensions 300 may be constructed by establishing one or more of these pairings of most similar in length conductors as measured from a given reference point where the two conductors of the pairing are given adequately balanced clocked positions. The adequately balanced clocked positions of one or more of these pairings then reduces the tendency of the end of the lead device 104 to curve and thereby improves the ability of the end of the lead device 104 to be inserted into a lead bore.

It will be appreciated that the implantable medical system 100 of FIG. 1 that utilizes lead devices having conductors on balanced clock positions may take many different forms. For instance, the implantable medical system 100 may be a neuromodulation device capable of produce stimulation signals that provide a neurological therapy such as spinal cord stimulation, deep brain stimulation, peripheral nerve stimulation, and the like. The implantable medical system 100 may be a cardiac device capable of providing pacing signals, defibrillation signals and the like. For any of these examples and for others not explicitly mentioned, the lead device 104 may utilize the balanced clocked conductor positions like those disclosed herein.

While embodiments have been particularly shown and described, it will be understood by those skilled in the art that various other changes in the form and details may be made therein without departing from the spirit and scope of the invention.

What is claimed is:

1. An implantable medical lead device, comprising:
   a lead device body;
   at least four proximal electrical connectors located on a proximal end of the lead device body and separated longitudinally;

at least four distal electrical connectors located on a distal end of the lead device body; and at least four conductors within the lead device body, wherein each of the conductors of the at least four conductors interconnects a corresponding proximal electrical connector of the at least four proximal electrical connectors to a corresponding distal electrical connector of the at least four distal electrical connectors, wherein each of the at least four conductors has a length as measured from a given longitudinal position along the lead device body where the at least four conductors are connected to the corresponding proximal electrical connector of each conductor, wherein the length of a first conductor of the at least four conductors is most similar among the at least four conductors to the length of a second conductor of the at least four conductors, and wherein the first conductor and the second conductor are clocked in positions providing an angular separation between the first conductor and the second conductor of at least 135 degrees.

2. The implantable medical lead device of claim 1, wherein the length of a third conductor of the at least four conductors is most similar among the at least four conductors to the length of a fourth conductor of the at least four conductors and wherein the third conductor and the fourth conductor are clocked in positions providing an angular separation between the third conductor and the fourth conductor of at least 135 degrees.

3. The implantable medical lead device of claim 2, wherein the at least four conductors comprise at least six conductors, and wherein the length of a fifth conductor of the at least six conductors is most similar among the at least six conductors to the length of a sixth conductor of the at least six conductors and wherein the fifth conductor and the sixth conductor are clocked in positions providing an angular separation between the fifth conductor and the sixth conductor of at least 135 degrees.

4. The implantable medical lead device of claim 1, wherein the proximal electrical connectors are rings.

5. The implantable medical lead device of claim 1, wherein the implantable medical lead device is an implantable lead extension that comprises a distal housing and wherein the distal electrical connectors are electrical contacts present within the distal housing and configured to receive lead proximal electrical connectors.

6. The implantable medical lead of claim 1, wherein each of the conductors of the plurality of conductors is linear at least for a proximal portion.

7. An implantable medical system, comprising:
an implantable medical stimulator device that includes a header having a lead bore and electrical contacts within the lead bore; and
an implantable medical lead device that comprises:
a lead device body;
at least four proximal electrical connectors located on a proximal end of the lead device body and separated longitudinally, the proximal end being located within the lead bore such that the at least four proximal electrical connectors are in contact with corresponding electrical contacts present within the lead bore;
at least four distal electrical connectors located on a distal end of the lead device body; and
at least four conductors within the lead device body, wherein each of the conductors of the at least four conductors interconnects a corresponding proximal electrical connector of the at least four proximal electrical connectors to a corresponding distal electrical connector of the at least four distal electrical connectors, wherein the at least four conductors has a length measured from a given longitudinal position along the lead device body where the at least four conductors are connected to the corresponding proximal electrical connector of each conductor, wherein the length of a first conductor of the at least four conductors is most similar among the at least four conductors to the length of a second conductor of the at least four conductors, and wherein the first conductor and the second conductor are clocked in positions providing an angular separation between the first conductor and the second conductor of at least 135 degrees.

8. The implantable medical system of claim 7, wherein the length of a third conductor of the at least for conductors is most similar among the at least four conductors to the length of a fourth conductor of the at least four conductors and wherein the third conductor and the fourth conductor are clocked in positions providing an angular separation between the third conductor and the fourth conductor of at least 135 degrees.

9. The implantable medical system of claim 8, wherein the at least four conductors comprise at least six conductors, and wherein the length of a fifth conductor of the at least six conductors is most similar among the at least six conductors to the length of a sixth conductor of the at least six conductors and wherein the fifth conductor and the sixth conductor are clocked in positions providing an angular separation between the fifth conductor and the sixth conductor of at least 135 degrees.

10. The implantable medical system of claim 7, wherein the implantable lead device is an implantable lead extension having a distal housing, wherein the proximal connectors are rings, wherein the distal electrical connectors are distal electrical contacts present within the distal housing, and wherein each of the conductors of the plurality of conductors is linear at least for a proximal portion, the implantable medical system further comprising an implantable medical lead having a proximal end with electrical connectors present within the distal housing and engaging the distal electrical contacts.

11. An implantable medical lead device, comprising:
a lead device body;
at least five proximal electrical connectors located on a proximal end of the lead device body and separated longitudinally;
at least five distal electrical connectors located on a distal end of the lead device body; and
at least five conductors within the lead device body, wherein each of the conductors of the at least five conductors interconnects a corresponding proximal electrical connector of the at least five proximal electrical connectors to a corresponding distal electrical connector of the at least five distal electrical connectors, wherein the at least five conductors has a length as measured from a given longitudinal position along the lead device body where the at least five conductors are connected to the corresponding proximal electrical connector of each conductor, wherein the length of a first conductor of the at least five conductors is most similar among the at least five conductors to the length of a second conductor of the at least five conductors, and wherein the first conductor and the second conductor are clocked in positions providing an angular separation between the first conductor and the second conductor of at least a quantity equal to 180 degrees less a second quantity equal to 360 degrees divided by a total number of conductors present within the lead device body.

12. The implantable medical lead device of claim 11, wherein the length of a third conductor of the at least five conductors is most similar among the at least five conductors to the length of a fourth conductor of the at least five conductors and wherein the third conductor and the fourth conductor are clocked in positions providing an angular separation between the third conductor and the fourth conductor of at least the quantity equal to 180 degrees less the second quantity.

13. The implantable medical lead device of claim 12, wherein the at least five conductors comprise at least six conductors, wherein the length of a fifth conductor of the at least six conductors is most similar among the at least six conductors to the length of a sixth conductor of the at least six conductors, and wherein the fifth conductor and the sixth conductor are clocked in positions providing an angular separation between the fifth conductor and the sixth conductor of at least the quantity equal to 180 degrees less the second quantity.

14. The implantable medical lead device of claim 11, wherein the proximal connectors are rings.

15. The implantable medical lead device of claim 11, wherein the implantable medical lead device is an implantable medical lead extension having a distal housing and wherein the distal electrical connectors are distal electrical contacts that are within the distal housing and are configured to receive proximal electrical connectors of an implantable medical lead.

16. The implantable medical lead device of claim 11, wherein each of the conductors of the plurality of conductors is linear at least for a proximal portion.

17. An implantable medical system, comprising:
an implantable medical stimulation device that includes a header having a lead bore and electrical contacts within the lead bore; and
an implantable medical lead device that comprises:
a lead device body;
at least five proximal electrical connectors located on a proximal end of the lead device body and separated longitudinally, the proximal end being located within the lead bore such that the at least five proximal electrical connectors are in contact with corresponding electrical contacts present within the lead bore;
at least five distal electrical connectors located on a distal end of the lead device body; and
at least five conductors within the lead device body, wherein each of the conductors of the at least five conductors interconnects a corresponding proximal electrical connector of the at least five proximal electrical connectors to a corresponding distal electrical connector of the at least five distal electrical connectors,
wherein each of the at least five conductors has a length as measured from a given longitudinal position along the lead device body where the at least five conductors are connected to the corresponding proximal electrical connector of each conductor,
wherein the length of a first conductor of the at least five conductors is most similar among the at least five conductors to the length of a second conductor of the at least five conductors,
and wherein the first conductor and the second conductor are clocked in positions providing an angular separation between the first conductor and the second conductor of at least a quantity equal to 180 degrees less a second quantity equal to 360 degrees divided by a total number of conductors present within the lead device body.

18. The implantable medical system of claim 17, wherein the length of a third conductor of the at least five conductors is most similar among the at least five conductors to the length of a fourth conductor of the at least five conductors and wherein the third conductor and the fourth conductor are clocked in positions providing an angular separation between the third conductor and the fourth conductor of at least the quantity equal to 180 degrees less the second quantity.

19. The implantable medical system of claim 18, wherein the at least four conductors comprise at least six conductors, wherein the length of a fifth conductor of the at least six conductors is most similar among the at least six conductors to the length of a sixth conductor of the at least six conductors, and wherein the fifth conductor and the sixth conductor are clocked in positions providing an angular separation between the fifth conductor and the sixth conductor of at least the quantity equal to 180 degrees less the second quantity.

20. The implantable medical system of claim 17, wherein the implantable medical lead device is an implantable medical lead extension having a distal housing, wherein the proximal connectors are rings, wherein the distal electrical connectors are distal electrical contacts within the housing, wherein each of the conductors of the plurality of conductors is linear at least for a proximal portion, and the implantable medical system further comprising an implantable medical lead having a proximal end with proximal electrical contacts that are within the distal housing and that engage corresponding electrical distal contacts.

21. A method of providing an implantable medical lead device, comprising:
providing a lead device body;
providing at least four proximal electrical connectors located on a proximal end of the lead device body and separated longitudinally;
providing at least four distal electrical contacts located on a distal end of the lead device body; and
inserting at least four conductors within the lead device body,
wherein each of the conductors of the at least four conductors interconnects a corresponding proximal electrical connector of the at least four proximal electrical connectors to a corresponding distal electrical connector of the at least four distal electrical connectors,
wherein each of the at least four conductors has a length as measured from a given longitudinal position along the lead device body where the at least four conductors are connected to the corresponding proximal electrical connector of each conductor,
wherein the length of a first conductor of the at least four conductors is most similar among the at least four conductors to the length of a second conductor of the at least four conductors,
and wherein the first conductor and the second conductor are clocked in positions providing an angular separation between the first conductor and the second conductor of at least 135 degrees.

22. A method of providing an implantable medical lead device, comprising:

provide a lead device body;

providing at least five proximal electrical connectors located on a proximal end of the lead device body and separated longitudinally;

providing at least five distal electrical connectors located on a distal end of the lead device body; and inserting at least five conductors within the lead device body, wherein each of the conductors of the at least five conductors interconnects a corresponding proximal electrical connector of the at least five proximal electrical connectors to a corresponding distal electrical connector of the at least five distal electrical connectors, wherein the at least five conductors has a length as measured from a given longitudinal position along the lead device body where the at least five conductors are connected to the corresponding proximal electrical connector of each conductor, wherein the length of a first conductor of the at least five conductors is most similar among the at least five conductors to the length of a second conductor of the at least five conductors, and wherein the first conductor and the second conductor are clocked in positions providing an angular separation between the first conductor and the second conductor of at least a quantity equal to 180 degrees less a second quantity equal to 360 degrees divided by a total number of conductors present within the lead device body.

* * * * *